(12) United States Patent
Caskey et al.

(10) Patent No.: US 9,718,750 B2
(45) Date of Patent: Aug. 1, 2017

(54) METHOD FOR SELECTIVE AND REGENERATIVE REMOVAL OF ACETALDEHYDE USING THERMALLY DECOMPOSED SODIUM ALUMINUM CARBONATE HYDROXIDE ON ALUMINA

(71) Applicant: UOP LLC, Des Plaines, IL (US)

(72) Inventors: Stephen Caskey, Lake Villa, IL (US); Vladislav I. Kanazirev, Arlington Heights, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 15/349,942

(22) Filed: Nov. 11, 2016

(65) Prior Publication Data

US 2017/0174594 A1 Jun. 22, 2017

Related U.S. Application Data

(60) Provisional application No. 62/268,167, filed on Dec. 16, 2015.

(51) Int. Cl.
| | |
|---|---|
| *C07C 29/00* | (2006.01) |
| *B01D 53/00* | (2006.01) |
| *B01J 20/00* | (2006.01) |
| *C10G 25/00* | (2006.01) |
| *C07C 29/76* | (2006.01) |
| *B01D 53/04* | (2006.01) |
| *C10G 25/12* | (2006.01) |
| *B01J 20/02* | (2006.01) |

(52) U.S. Cl.
CPC .......... *C07C 29/76* (2013.01); *B01D 53/0462* (2013.01); *B01J 20/0248* (2013.01); *C10G 25/003* (2013.01); *C10G 25/12* (2013.01); *B01D 2253/104* (2013.01); *B01D 2253/1122* (2013.01); *B01D 2253/25* (2013.01); *B01D 2256/24* (2013.01); *B01D 2257/708* (2013.01); *B01D 2259/4009* (2013.01); *C10G 2300/202* (2013.01)

(58) Field of Classification Search
CPC .. C07C 29/76; B01D 53/0462; B01J 20/0248; C10G 25/00
See application file for complete search history.

(56) References Cited

U.S. PATENT DOCUMENTS 7,758,837 B2 * 7/2010 Kanazirev .............. B01D 53/02
423/240 S

FOREIGN PATENT DOCUMENTS

| CN | 103523796 A | 1/2014 |
|---|---|---|
| CN | 102921373 B | 12/2014 |
| JP | 2006055678 A | 3/2006 |

* cited by examiner

*Primary Examiner* — Sikarl Witherspoon

(57) ABSTRACT

A process is presented for the removal of acetaldehyde from mixture of oxygenates. Acetaldehyde is selectively removed in the presence of other oxygenates like ketones, alcohols and nitriles using an amorphous sodium doped alumina derived from thermally decomposed Dawsonite. The process successfully removes acetaldehyde which can adversely impact catalyst operation.

14 Claims, No Drawings

METHOD FOR SELECTIVE AND REGENERATIVE REMOVAL OF ACETALDEHYDE USING THERMALLY DECOMPOSED SODIUM ALUMINUM CARBONATE HYDROXIDE ON ALUMINA

CROSS-REFERENCE TO RELATED APPLICATION

This application claims priority from Provisional Application No. 62/268,167 filed Dec. 16, 2015, the contents of which are hereby incorporated by reference.

BACKGROUND

The present subject matter relates generally to method for the removal of acetaldehyde in the presence of other oxygenates from feedstocks. More specifically, it relates to methods for the removal of acetaldehyde using an amorphous sodium-doped alumina derived from thermally decomposed Dawsonite (sodium aluminum carbonate hydroxide).

Feedstocks derived from fluid catalytic cracking processes used in industry should be produced to be as pure as possible without the presence of contaminants. Conventionally, acetaldehyde is a common contaminant in C4 fractions of such feedstocks. The purification of the feedstock is needed for many refining and petrochemical applications. Acetaldehyde is known to be particularly problematic toward downstream catalytic processes due to a potential for condensation and polymerization reactions. Furthermore, acetaldehyde is a health hazard to humans as a possible or probable carcinogen. High acetaldehyde contamination can lead to deactivation of zeolite based adsorbents towards removal of other contaminants due to preferential adsorption of acetaldehyde.

Adsorbents selective to adsorb oxygen containing organic compounds are typically known in the prior art. The oxygen containing organic compounds include various contaminants such as aldehydes, ketones, esters, alcohols, etc. The conventionally employed adsorbents are not effective for efficient removal of acetaldehyde. The selective removal of acetaldehyde has been difficult to achieve with zeolite based adsorbents due to their affinities to various oxygenates that may be present along with the acetaldehyde contaminant in the feedstock. The presence of acetaldehyde renders the feedstock undesirable for many commercial applications. Therefore, there is a need for an improved adsorbent that is selective for removal of acetaldehyde in the presence of other oxygenates as well as nitriles which also are usually preferentially adsorbed to acetaldehyde.

SUMMARY

An embodiment of the subject matter is a process for removal of acetaldehyde from a mixture of oxygenates comprising passing the mixture of oxygenates through an adsorbent bed. The acetaldehyde is preferentially removed as compared to other oxygenates from said mixture. The adsorbent bed comprises an adsorbent comprising an active amorphous sodium doped alumina.

Another embodiment of the subject matter is a process for removal of acetaldehyde from a hydrocarbon stream comprising passing the hydrocarbon stream through an adsorbent bed. An adsorbent in the adsorbent bed is a thermally activated sodium aluminum carbonate hydroxide.

Dawsonite is a sodium aluminum carbonate hydroxide, $NaAlCO_3(OH)_2$, which is formed upon curing a mixture of either sodium acetate or trona (sodium sesquicarbonate) and flash calcined alumina and water. The thermal activation of Dawsonite results in an amorphous Na-doped alumina phase that is generated by loss of carbon dioxide and water. This phase is active for regenerative acetaldehyde removal with minimal removal of other oxygenates and nitrile contaminants. The capacity for acetaldehyde is modest but acceptable since it can be regenerated by thermal activation.

The present invention seeks to provide a process for removal of acetaldehyde from a mixture of oxygenates. A benefit of the present subject matter is a process that enables use of an adsorbent that is selective for removal of acetaldehyde in the presence of other oxygenates and nitriles. These and other features, aspects, and advantages of the present subject matter will become better understood upon consideration of the following detailed description and appended claims.

DETAILED DESCRIPTION

The feedstocks derived from fluid catalytic cracking processes need to be purified for further processing and commercial applications. The C4 fraction of a feedstock is generally contaminated with acetaldehyde and other oxygenates. Acetaldehyde inhibits chemical reactions by deactivating the zeolite based adsorbents that may be used to remove other contaminants. The presence of acetaldehyde is known to affect the downstream catalytic process. Therefore, acetaldehyde is an undesirable contaminant that needs to be removed from feedstocks to meet the product specification for commercial use.

Typically, adsorbents are used to adsorb oxygenates from oxygenate containing mixtures. But these adsorbents are not effective for selective removal of acetaldehyde in the presence of other oxygenates. Selective removal of acetaldehyde is difficult to achieve with commonly used adsorbents like zeolites due to their affinities to various oxygenates. The present invention provides a novel method to selectively remove acetaldehyde from oxygen containing mixtures. An amorphous sodium doped alumina from thermally decomposed Dawsonite that is active for regenerative removal of acetaldehyde is used with minimal removal of other oxygenate and nitrile contaminants.

The composite sorbents prepared according to the present invention have significant advantages over the prior art since they are low cost materials exhibiting high BET surface area and porosity along with a high content of active component. A further advantage is that the sorbents do not require a separate binder to be added to the mixture in the forming process. They have sufficient mechanical stability in both fresh and spent state along with low reactivity towards the main stream. The present invention comprises a process for removing acetaldehyde from a mixture of oxygenates using the adsorbent prepared according to the process disclosed below.

At least two solid and one liquid components are needed to produce the reactive composite sorbent of the present subject matter. At least one carbonate powder and at least one alumina powder comprise the solid components and water or an aqueous solution of at least one salt is the liquid component.

The carbonate powder is preferably an alkali metal carbonate in a powder form. Small particles, preferably about 5 to 10 microns in diameter, are employed. A carbonate component that has been found to provide excellent results in the present invention is the natural carbonate (soda ash) ore known as Trona or Nahcolite. A popular source of such natural carbonate is the Green River occurrence in Wyoming, U.S. The book Natural Soda Ash: Occurrences, Processing and Use, authored by Donald E. Garrett, Van Nostrand Reinhold publication, 1992, summarizes important characteristics of natural carbonates. Other carbonates that can be used include Wegscheiderite ($Na_2CO_3 \cdot NaHCO_3$), Thermonatrite ($Na_2CO_3 \cdot H_2O$), Shortite ($Na_2CO_3 \cdot 2CaCO_3$), and Eitelite ($Na_2CO_3 \cdot MgCO_3$).

One such carbonate that has been found especially useful is a natural sodium sesquicarbonate, marketed by Solvay Chemicals, Houston, Tex. as Solvay T-200®. A sesquicarbonate has a formula of $NaAlCO_3(OH)_2$. It produces 1.5 mols sodium carbonate ($Na_2CO_3$) upon heating at sufficiently high temperature. Table 1 presents some properties of this product as reflected in the producer's technical data sheet.

TABLE 1

| Component | Typical Analysis |
|---|---|
| $NaAlCO_3(OH)_2$ | 97.5% |
| Free Moisture | 0.01 |
| Water Insoluble | 2.3% |
| NaCl | 0.1 |
| Bulk Density | 785 kg/m$^3$ (49.0 lbs/ft$^3$) |

| Sieve Opening, micrometers | Weight Percent |
|---|---|
| <70 | 75 |
| <28 | 50 |
| 6 | 10 |

The carbonate raw material was found to have a typical FTIR (Fourier Transform Infrared) spectrum characterized with absorbance peaks at about 3464, 3057, 1697, 1463, 1190, 1014, 850 and 602 cm-1, corresponding to the values published for this material.

An alumina powder that has been found to be useful in the present invention is a transition alumina powder produced by the rapid calcination of $Al(OH)_3$, known as Gibbsite. Alumina A-300, sold by UOP LLC, Des Plaines, Ill., is a typical commercial product that is suitable as a component of the reactive composite of the present invention. This alumina powder has a BET surface area of about 300 m$^2$/g and about 0.3 wt-% $Na_2O$. It contains only a few percent free moisture and is capable of fast rehydration in the presence of water. The FTIR spectrum of A-300 has the broad absorbance peaks due to Al—O vibration at about 746 and 580 cm-1, with only a few additional peaks of OH (3502 and 1637 cm-1) and $CO_3$ of surface carbonate species (1396 and 1521 cm-1) are present.

The third component is water, or optionally an aqueous solution of a salt, which plays an important role in facilitating a reaction between the carbonate and alumina powder. The preferred salts include metal salt is selected from the group consisting of sodium acetate, sodium oxalate and sodium formate. The preferred average particle size D50 for the alumina component and the carbonate ingredient is from about 5 to 12 μm, although larger particles may be used, especially for the carbonate ingredient. The alumina and the sesquicarbonate are present in a ratio of about 0.8 to about 5. Preferably, the alumina and the sesquicarbonate are present in a ratio of about 2 to 4.

It has been found that that there is no reaction between the sesquicarbonate and alumina when a mixture is heated in a dry state to about 100° C. However, heating the dry mix to a an initial temperature of from 300° C. up to 600° C. converts the sesquicarbonate to sodium carbonate. In contrast, the presence of additional water followed by brief calcination at 100° C. triggers a reaction between the sesquicarbonate and alumina. The product was found to be Dawsonite crystals having a particle size of less than about 200 angstroms. Example 1 describes the process to produce this phenomenon.

EXAMPLE 1

About 19 g T-200® sesquicarbonate powder and 45 g A-300 alumina were placed in a small rotating pan made from the bottom of a plastic bottle. The pan has a diameter of about 12.7 cm (5 inches) and a height of about 15.2 cm (6 inches). It rotated at about 120 rpm at an inclination of about 45 degrees. The powder was occasionally stirred using a spatula and hand sprayed with water to form particulates. A total of about 16.25 g water was added before the particulates began to stick together, At that point the addition of water ceased and a small amount of additional A-300 powder was added in order to restore the free flowing pattern of particulates.

The particulates had a broad particle size distribution ranging from about 40 mesh to about 3 mesh. Other than some spherical beads, most of the particles had a rather irregular form.

All particulates were placed in a closed glass container and allowed to cure for about 2 hours followed by calcination at 100° C. for about 3 hours in an air circulated oven. The material lost about 27.3% of its weight upon calcination. After cooling, the size fraction 7×20 mesh of the particulates was screened out for further testing, FTIR and acetaldehyde pickup in particular.

It was found that the carbonate and alumina components reacted in presence of water upon formation of a product that was identified as similar in spectra to aluminum containing hydroxycarbonate Dawsonite—$NaAlCO_3(OH)_2$. The identification is based on the characteristic vibrations in the spectrum compared with the reference published by P. A. Estep and C. Karr, Jr. in "The Infrared Spectrum of Dawsonite", American Mineralogist, 53, 305 (1968). The consumption of alumina in the course of reaction is evident by the decrease of the absorbance at about 746 cm-1. The spectrum of the product had characteristic absorbance peaks at 3290, 1560, 1398, 1097, 956, 846, 684 and 548 cm-1. At least five of these peaks would be seen. Independently, the FTIR identification of the reaction product was confirmed on a similar material by X-ray diffraction. The X-ray patterns (CuKα1 radiation) show characteristic peaks at about 5.68, 2.78, 2.61, 2.15 and about 1.73 angstroms (or about 15.60, 32.02, 34.25, 41.94, 52.74 if expressed as 2θ angles). The width at the half height of the most intense peak at about 15.60 two θ angle was about 0.96 degree 2θ which would correspond to the 85 Å crystal size of Dawsonite.

EXAMPLE 2

A portion of this sample was additionally heated for 2 hours at 315° C. in the air circulated oven. The sample lost 15.2% weight upon this treatment. This loss in weight indicates a partial decomposition of the Dawsonite precursor. The FTIR spectrum of the product showed that another yet unidentified carbonate compound still remained in the final product.

The present subject matter provides a process for removal of acetaldehyde in the presence of other oxygenates such as alcohols, ketones and nitriles using an amorphous Na-doped alumina derived from thermally decomposed Dawsonite in a regenerative two swing or three swing, lead-lag configuration of adsorbent beds. The feed mixture of oxygenates is passed through an adsorbent bed that comprises an adsorbent comprising an active amorphous sodium doped alumina. The acetaldehyde is preferentially removed as compared to other oxygenates from the feed mixture. The feed may comprise other reactive components such as olefins, acetylenes, or dienes as shown in the Table 2 below.

TABLE 2

| Compound | Boiling Point (° C.) | Concentration (ppm) |
| --- | --- | --- |
| Propadiene | −34 | 650 |
| Methyl acetelyene | −23 | 1350 |
| Isobutane | −12 | balance |
| Isobutylene | −7 | 10000 |
| Acetaldehyde | 20 | 200 |
| Acetone | 57 | 800 |
| Methanol | 65 | 200 |
| t-Butanol | 82 | 600 |
| Propionitrile | 97 | 200 |

Dawsonite may be generated by curing a mixture of a sodium source and alumina in the presence of water and carbon dioxide. Dawsonite is then thermally decomposed to active amorphous Na-doped alumina phase. The active amorphous sodium doped alumina is a thermal decomposition product of a sodium aluminum carbonate hydroxide Process variables typically include pre-treating sorbent for about 4 hours at about 250° C. in nitrogen flow. The adsorbent is loaded in gas phase at about 0.4 ml at about 1.5 g/hr feed (~3 WHSV) at temperature of about 60° C. and pressure of about 75 psig. The active amorphous sodium doped alumina content can range from about 1% to about 30%, and preferably in the range of about 4% to about 15% on a sodium oxide (Na2O) basis on alumina. The breakthrough capacity observed for a given condition with around 12% sodium oxide (Na2O)/alumina sample was about 1.4 wt % of acetaldehyde removed at breakthrough for the first cycle and about 0.8 wt % of acetaldehyde removed at breakthrough for the third cycle. Breakthrough capacity is defined as the capacity at which the effluent concentration is 10% of the feed concentration. The saturation capacity is defined as the capacity at which the effluent concentration is 90% of the feed concentration. The Table 3 below shows good regenerative capacity for acetaldehyde with 12% $Na_2O$/alumina, an amorphous sodium doped alumina generated analogously to Example 2.

TABLE 3

| | | 12% $Na_2O$/alumina | |
| --- | --- | --- | --- |
| Wt % capacities cycle | Contaminant | $1^{st}$ cycle | $3^{rd}$ cycle |
| Breakthrough | Methanol | 0.3 | 0.3 |
| Breakthrough | acetaldehyde | 1.4 | 0.8 |
| Breakthrough | Acetone | 0.5 | 0.3 |
| Breakthrough | Propionitrile | 0.1 | 0.1 |
| Breakthrough | t-butanol | 0.5 | 0.2 |
| Saturation | Methanol | 0.4 | 0.3 |
| Saturation | acetaldehyde | 2.1 | —* |
| Saturation | Acetone | 1.2 | 0.5 |
| Saturation | Propionitrile | 0.1 | 0.1 |
| Saturation | t-butanol | 0.6 | 0.2 |

*saturation was not achieved in the $3^{rd}$ cycle due to long mass transfer zone There are other practical ways to produce the composite sorbent of the present subject matter. One of the possible approaches involves preparing pellets of the solid mix followed by contacting the pellets with liquid. Application of known extrusion techniques is another approach. Another approach, especially effective in case of scavengers with low content of active component, is preparing a solution of the natural carbonate and contacting this solution with a preformed macroporous support. Increased temperature can be used to accommodate more alkali metal into solution. The thermally activated sodium aluminum carbonate hydroxide may be regenerated using a thermal swing adsorption process.

The method of the present subject matter is unique since the solid components reacts during the forming and curing steps to produce a different compound. This compound and the products of its thermal decomposition are useful for selective removal of acetaldehyde from a mixture of oxygenates and nitriles.

While the subject matter has been described with what are presently considered the preferred embodiments, it is to be understood that the subject matter is not limited to the disclosed embodiments, but it is intended to cover various modifications and equivalent arrangements included within the scope of the appended claims.

SPECIFIC EMBODIMENTS

While the following is described in conjunction with specific embodiments, it will be understood that this description is intended to illustrate and not limit the scope of the preceding description and the appended claims.

A first embodiment of the invention is a process for removal of acetaldehyde from a mixture of oxygenates through an adsorbent bed; removing acetaldehyde preferentially as compared to other oxygenates from the said mixture; and wherein the adsorbent bed comprises an adsorbent comprising an active amorphous sodium doped alumina. An embodiment of the invention is one, any or all of prior embodiments in this paragraph up through the first embodiment in this paragraph wherein said active amorphous sodium doped alumina is a thermal decomposition product of a sodium aluminum carbonate hydroxide. An embodiment of the invention is one, any or all of prior embodiments in this paragraph up through the first embodiment in this paragraph wherein said active amorphous sodium doped alumina comprises from about 1% to about 30% Na on a Na2O basis on alumina. An embodiment of the invention is one, any or all of prior embodiments in this paragraph up through the first embodiment in this paragraph wherein said active amorphous sodium doped alumina comprises from about 4% to about 15% Na on a $Na_2O$ basis on alumina. An embodiment of the invention is one, any or all of prior embodiments in this paragraph up through the first embodiment in this paragraph wherein said active amorphous sodium doped alumina comprises from about 12% Na on a $Na_2O$ basis on alumina. An embodiment of the invention is one, any or all of prior embodiments in this paragraph up through the first embodiment in this paragraph wherein said other oxygenates are selected from the group consisting of alcohols, ethers, and ketones.

A second embodiment of the invention is a process for removal of acetaldehyde from a hydrocarbon stream comprising passing said hydrocarbon stream through an adsorbent bed; and wherein an adsorbent in the adsorbent bed contains a thermally activated sodium aluminum carbonate hydroxide. An embodiment of the invention is one, any or all of prior embodiments in this paragraph up through the second embodiment in this paragraph wherein a greater proportion of acetaldehyde from said hydrocarbon stream is adsorbed than other oxygenates or nitriles from said hydrocarbon stream. An embodiment of the invention is one, any or all of prior embodiments in this paragraph up through the second embodiment in this paragraph wherein said thermally activated sodium aluminum carbonate hydroxide is an active amorphous sodium doped alumina. An embodiment of the invention is one, any or all of prior embodiments in this paragraph up through the second embodiment in this paragraph wherein at least 80% of the acetaldehyde is removed from the hydrocarbon stream. An embodiment of the invention is one, any or all of prior embodiments in this paragraph up through the second embodiment in this paragraph wherein said thermally activated sodium aluminum carbonate hydroxide is regenerated in a thermal swing adsorption process. An embodiment of the invention is one, any or all of prior embodiments in this paragraph up through the second embodiment in this paragraph wherein said thermal swing process uses a heated gas at a temperature between about 100° and 350° C. for regeneration. An embodiment of the invention is one, any or all of prior embodiments in this paragraph up through the second embodiment in this paragraph wherein wherein said heated gas is at a temperature between 150° and 250° C. for regeneration. An embodiment of the invention is one, any or all of prior embodiments in this paragraph up through the second embodiment in this paragraph wherein said heated gas is at a temperature of about 230° C. regeneration.

Without further elaboration, it is believed that using the preceding description that one skilled in the art can utilize the present invention to its fullest extent and easily ascertain the essential characteristics of this invention, without departing from the spirit and scope thereof to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

The invention claimed is:

1. A process for removal of acetaldehyde from a mixture of oxygenates comprising passing said mixture of oxygenates through an adsorbent bed;
    removing acetaldehyde preferentially as compared to other oxygenates from the said mixture; and
    wherein the adsorbent bed comprises an adsorbent comprising an active amorphous sodium doped alumina.

2. The process of claim 1 wherein said active amorphous sodium doped alumina is a thermal decomposition product of a sodium aluminum carbonate hydroxide.

3. The process of claim 1 wherein said active amorphous sodium doped alumina comprises from about 1 to about 30% Na on a $Na_2O$ basis on alumina.

4. The process of claim 1 wherein said active amorphous sodium doped alumina comprises from about 4 to about 15% Na on a $Na_2O$ basis on alumina.

5. The process of claim 1 wherein said active amorphous sodium doped alumina comprises about 12% Na on a $Na_2O$ basis on alumina.

6. The process of claim 1 wherein said other oxygenates are selected from the group consisting of alcohols, ethers, and ketones.

7. A process for removal of acetaldehyde from a hydrocarbon stream comprising passing said hydrocarbon stream through an adsorbent bed; and
    wherein an adsorbent in the adsorbent bed contains a thermally activated sodium aluminum carbonate hydroxide.

8. The process of claim 7 wherein a greater proportion of acetaldehyde from said hydrocarbon stream is adsorbed than other oxygenates or nitriles from said hydrocarbon stream.

9. The process of claim 7 wherein said thermally activated sodium aluminum carbonate hydroxide is an active amorphous sodium doped alumina.

10. The process of claim 7 wherein at least 80% of said acetaldehyde is removed from said hydrocarbon stream.

11. The process of claim 7 wherein said thermally activated sodium aluminum carbonate hydroxide is regenerated in a thermal swing adsorption process.

12. The process of claim 7 wherein said thermal swing process uses a heated gas at a temperature between about 100° and 350° C. for regeneration.

13. The process of claim 12 wherein said heated gas is at a temperature between 150° and 250° C. for regeneration.

14. The process of claim 12 wherein said heated gas is at a temperature of about 230° C. regeneration.

* * * * *